United States Patent
Vergnes et al.

(10) Patent No.: US 8,082,114 B2
(45) Date of Patent: Dec. 20, 2011

(54) METHOD FOR CHARACTERIZING THE ENDURANCE LIMIT OF A PART FROM ITS SURFACE PROFILE

(75) Inventors: Vivian Vergnes, Tournefeuille (FR);
Remy Chieragatti, Caraman (FR);
Catherine Mabru, Toulouse (FR);
Christine Espinosa, Tournefeuille (FR);
Monchai Surarachai, Toulouse (FR)

(73) Assignee: Airbus Operations SAS, Toulouse (FR)

( * ) Notice: Subject to any disclaimer, the term of this patent is extended or adjusted under 35 U.S.C. 154(b) by 0 days.

(21) Appl. No.: 12/281,842

(22) PCT Filed: Mar. 6, 2007

(86) PCT No.: PCT/FR2007/000395
§ 371 (c)(1),
(2), (4) Date: Sep. 5, 2008

(87) PCT Pub. No.: WO2007/101939
PCT Pub. Date: Sep. 13, 2007

(65) Prior Publication Data
US 2009/0093976 A1      Apr. 9, 2009

(30) Foreign Application Priority Data
Mar. 7, 2006   (FR) ................................... 06 50793

(51) Int. Cl.
*G01B 3/44*     (2006.01)
*G06F 19/00*    (2006.01)
(52) U.S. Cl. ............................................. 702/34

(58) Field of Classification Search .............. 702/33–36, 702/42, 81, 83–85, 150–155, 167, 170; 73/105, 73/865.8, 799; 324/456; 703/2, 7, 6
See application file for complete search history.

(56) References Cited

U.S. PATENT DOCUMENTS

| 4,860,589 | A  |   | 8/1989  | Williford          |         |
|-----------|----|---|---------|--------------------|---------|
| 4,973,164 | A  | * | 11/1990 | Weber et al.       | 356/600 |
| 5,133,601 | A  | * | 7/1992  | Cohen et al.       | 356/497 |
| 5,204,734 | A  | * | 4/1993  | Cohen et al.       | 356/497 |
| 6,444,290 | B1 | * | 9/2002  | Takahashi et al.   | 428/141 |

(Continued)

FOREIGN PATENT DOCUMENTS
JP   9 304131     11/1997
WO   89 05448     6/1989

OTHER PUBLICATIONS

Andrews, S. et al., "A computer model for fatigue crack growth from rough surfaces", International Journal of Fatigue, vol. 22, No. 7, XP002419361, pp. 619-630, (2000).

(Continued)

*Primary Examiner* — Cindy Hien-Dieu Khuu
(74) *Attorney, Agent, or Firm* — Oblon, Spivak, McClelland, Maier & Neustadt, L.L.P.

(57) ABSTRACT

The invention concerns a method for characterizing the endurance limit of a part from the state of its surface including the following steps: reading geometrical data describing the surface profile of the zone the endurance limit of which is to be determined, applying said data to a computing model so as to work out an estimate of the field of mechanical stresses in said zone of said part, deducing from said estimate of the field of stresses at least one quantity characteristic of the endurance behavior of the part.

12 Claims, 9 Drawing Sheets

U.S. PATENT DOCUMENTS

| | | | |
|---|---|---|---|
| 7,230,421 B2* | 6/2007 | Goldfine et al. | 324/240 |
| 2003/0106378 A1* | 6/2003 | Giannakopoulos et al. | 73/788 |
| 2003/0173958 A1* | 9/2003 | Goldfine et al. | 324/209 |
| 2004/0224179 A1* | 11/2004 | Sokol et al. | 428/610 |
| 2004/0234154 A1* | 11/2004 | Hier | 382/254 |
| 2006/0082366 A1* | 4/2006 | Goldfine et al. | 324/240 |
| 2006/0243035 A1* | 11/2006 | Aoki | 73/105 |
| 2007/0005295 A1* | 1/2007 | Dusserre-Telmon et al. | 702/167 |
| 2007/0213942 A1* | 9/2007 | Ponson et al. | 702/36 |
| 2008/0123106 A1* | 5/2008 | Zeng et al. | 356/600 |
| 2009/0315540 A1* | 12/2009 | Goldfine et al. | 324/202 |

OTHER PUBLICATIONS

Sehitoglu, H. et al., "Contact of Crack Surfaces during Fatigue: Part 2. Simulations", Metallurgical and Materials Transactions A, vol. 28A, No. 11, pp. 2277-2289, XP009078707, (1997).

* cited by examiner

→ The acquired profile → The modified profile

METHOD FOR CHARACTERIZING THE ENDURANCE LIMIT OF A PART FROM ITS SURFACE PROFILE

FIELD OF THE INVENTION

The invention relates to characterizing the fatigue strength of a part on the basis of its surface state.

Fatigue damage is a practical problem that is encountered in all types of parts subjected to a range of cyclic loading. In this connection, the methods for manufacturing such parts cause fluctuations in the surface properties and therefore in the strength of fatigued parts. It is effectively known that the fatigue strength of mechanical parts depends in particular on their surface, where incipient fatigue cracks can appear.

The majority of studies on the influence of surface state of a part on its fatigue strength focus on 3 parameters for characterizing it:
 a geometric parameter,
 a metallurgical parameter, and/or
 a mechanical parameter.

Each parameter acts differently depending on the material, so that it is generally possible to choose one as being the most representative for a given material.

In certain cases, such as the aluminum alloy for aeronautical applications mainly of interest here, the most representative criterion is the geometric criterion. This criterion is related to the form of the surface roughness profile generated by the machining process. It is then common practice to apply a mechanical model to the geometric parameters identified in this way in order to estimate their influence on the fatigue strength.

PRIOR ART

Figure 1:
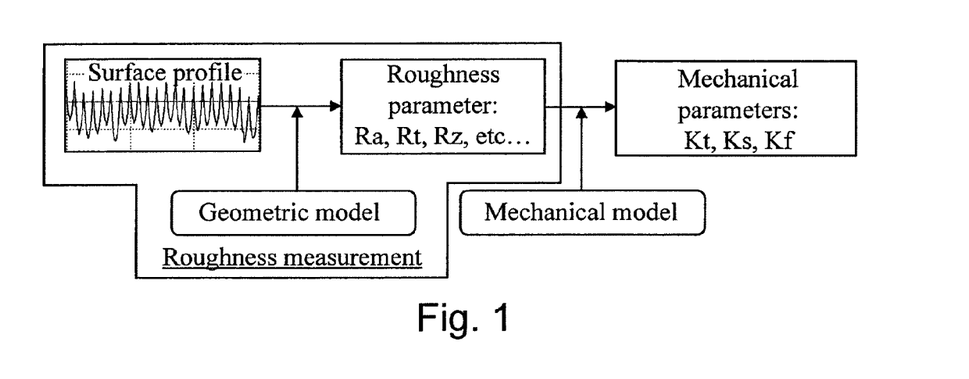
FIG. 1 is a diagram schematically illustrating the steps of characterization of the fatigue strength of a part on the basis of its surface profile.

Among the studies on the influence of surface states on fatigue strength, those devoted to the influence of geometry use geometric models that define roughness parameters. These are intermediate means of describing the surface; mechanical models effectively begin from this geometric description with these roughness parameters, to estimate their influence on the fatigue strength. The diagram of FIG. 1 schematically illustrates this approach.

1) Geometric Model:

The roughness parameters are calculated by the geometric model, by applying physical criteria or statistical criteria to a surface profile (see International Standard ISO 4287/1-1984 (E/F/R) (1984)). This step is generally effected by a roughness-measuring machine. Among the roughness parameters, those most often employed for subsequent determination of the fatigue strength of parts are:

The roughness average (Ra), which is the surface between the roughness profile and its average line, or the integral of the absolute value of the height of the roughness profile above the evaluation length:

$$R_a = \frac{1}{l} \int_0^l |Z(x)| dx$$

The peak-to-valley height (Rt), which is a vertical distance between the highest point and the lowest point of the roughness profile over the total evaluation length.

Figure 2:
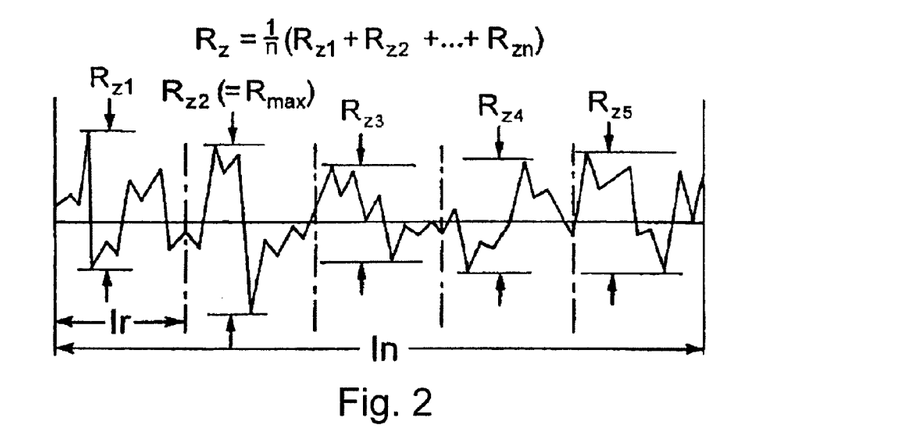
FIG. 2 is a diagram showing the roughness coefficient denoted Rz.

The average peak-to-valley roughness (Rz), which is the value of the arithmetic average of the simple depths Rzi of consecutive sampling lengths (the symbol "i" designating the consecutive lengths that can be identified as exhibiting peaks in the surface profile—see FIG. 2).

$$R_z = \frac{1}{n}(R_{z1} + R_{z2} + \ldots + R_{zn})$$

2) Mechanical Model:

Roughness parameters obtained in this way are then used by different known models in order to determine the mechanical properties. These models can be divided into 2 categories:
 models of surface factor (Ks), and
 models of the influence of roughness on fatigue strength 2.1) Modeling of the factor Ks:

The factor Ks is defined as the ratio of the endurance limit of the given test specimen having a certain surface roughness and the endurance limit of a control specimen whose surface state is chosen as reference:

$$K_s = \frac{\sigma_{DS}}{\sigma_D}$$

$\sigma_D$: fatigue limit of the specimen whose surface state is chosen as reference.

$\sigma_{DS}$: fatigue limit of the given test specimen having a certain surface roughness.

Several models have been proposed to define the value of Ks, known as "surface state factor".

Stieler (1954), using as basis the theory of stress concentration at geometric defects, proposed a formula of the type $$Ks = \frac{\left[1 + 2\sqrt{\frac{1}{C}} + \sqrt{\frac{1}{R}}\right]}{\left[1 + 2\sqrt{\frac{1}{C}}\right]}$$

where
 C: is a factor that depends on the machining,
 R: is defined as being equal to 2 Rt/Sg
 where Sg: represents the maximum thickness of material involved in the process of initiation of a fatigue crack. In a rotary bending test, Stieler showed that it is on the order of magnitude of the dimension of material grains.

Niemann and Glaubitz (1952) modeled their experimental results obtained in plane bending by formulas of the type:

$$\frac{\sigma_{DS}}{\sigma_D} = \left[\frac{Rt}{Rts}\right]^n$$

where:
 Rts: is the roughness of the given test specimen having a certain surface roughness,
 Rt: is the roughness of the reference specimen,
 σD: is the endurance limit of the reference specimen,
 σDS: is the endurance limit of the test specimen under consideration,
 n: is a coefficient that is a function of the material.

Brand et al. (CETIM, 1980) constructed a nomogram by smoothing a large number of available data, resulting in lines of negative slope giving Ks (the surface state factor) as a function of tensile strength Rm for diverse values of the roughness criterion Rt.

2.2) Modeling of the influence of roughness on fatigue strength:

Two approaches are generally used to predict the fatigue life as a function of roughness:
- an approach based on the notch effect,
- an approach based on fracture mechanics.

2.2.1) Notch effect

The approach based on the notch effect is derived from the traditional definition of the effective stress concentration factor Kf, which is the ratio of the endurance limit σD of a smooth test specimen to the endurance limit σD of a notched test specimen. This coefficient Kf is generally smaller than the theoretical stress concentration coefficient Kt. Some authors, notably Neuber, 1957, Smith et al., 1970, have proposed equations relating Kf to the factor Kt. For low values of Kt, Peterson (1959) has established an empirical relation defining the factor Kf as follows:

$$K_f = 1 + (K_t - 1)\left[1 + \frac{\alpha}{\rho}\right]$$

where Kt: is the stress concentration factor, $$\alpha = 0.0254 \left[\frac{2070}{Rm}\right]^{1.8}$$

α: is a constant related to the material
ρ: is the notch radius.

Arola and Williams (2002) expressed Kt as a function of the roughness parameters Ra, Rt and Rz and of the mean radius ρ at the notch bottom, and of a parameter n, which is a factor that depends on the type of loading (n=1 for loading in shear, n=2 for loading in uniform tension).

$$K_t = 1 + n\left(\frac{R_a}{\rho}\right)\left(\frac{R_t}{R_z}\right)$$

This factor Kt is then used to establish an empirical relation defining the factor Kf.

2.2.2) Fracture mechanics

Considering that the surface roughness forms notches that may be treated as cracks, it is possible to use the results of fracture mechanics. The fatigue behavior is then characterized by ΔKth, which is the variation of the threshold of the stress intensity factor. Kitagawa (1976) then plotted the evolution of this threshold ΔKth as a function of crack length in a log-log diagram in which the reference fatigue limit (on a polished specimen) is distinguished by a horizontal line, then a threshold curve that appears as a line of slope −½. The transition between these lines defines a zone in which the experimental data deviate from the theoretical curves.

Taylor and Clancy (1991) compared these curves with the roughness criterion Rmax, the predictions made by these two approaches with the experimental results. They concluded that the fracture mechanics approach is well suited to small roughness values, whereas the notch effect approach yields better results for large roughness values. The value of Rmax corresponding to the intersection of these two theoretical curves may provide a limit of validity of the prediction based on fracture mechanics, which becomes too conservative beyond this. In all cases, they believe that Rmax is the most significant surface criterion. In effect, this criterion satisfactorily represents either the depth of the largest notch (notch effect) or the largest length of the crack (fracture mechanics).

Andrews and Sehitogiu (2000) were interested in crack propagation and in the stress concentration factors present, making a distinction as to whether the cracks are considered to be short or long. They then proposed a stress concentration equation that takes into account relaxation of the stress concentrations when the notches are side-by-side.

2.3) Comments

In practice, the fatigue strength of parts may be influenced by the geometric surface profile among other factors. Irregularities of form of this profile influence the initiation or propagation of fatigue cracks. Nevertheless, the models that take them into account start not from the real form of these irregularities but from simplified geometric descriptions of profilometric measurements. The parameters obtained from these descriptions are numerous, but none of them makes it possible to ensure, for all types of irregularity, that the mechanical model using it is pertinent. Sometimes it is advisable to use one and sometimes the other, and only experience makes it possible to make a decision a posteriori. That therefore does not permit characterization of the fatigue strength without having undertaken preliminary tests.

The object of the invention is a new procedure for characterizing the fatigue strength of a part as a function of its surface state, making it possible to dispense with any purely geometric description of this profile (by the traditional parameters such as the roughness coefficients Ra, Rt, Rz, etc.), to focus instead on a mechanical description of the part in more direct relationship with the fatigue strength of the part under consideration.

DESCRIPTION OF THE INVENTION

According to one aspect of the invention, the 2D or 3D surface profile obtained by current roughness-measuring machines is first digitized, in order to calculate directly modifications of the local stress field generated at the surface by this profile. It therefore involves establishing a sequence for measuring a mechanical criterion associated with the geometry of a surface to assess it in terms of fatigue.

The invention therefore proposes a method for characterizing the fatigue strength of a part on the basis of its surface state, comprising the following steps:
- geometric data are recorded that describe the surface profile of the zone in which the fatigue strength is to be determined,
- these data are applied to a calculation model so as to formulate an estimate of the mechanical stress field in the said zone of the said part,
- at least one quantity characteristic of the fatigue behavior of the part is deduced from this estimate of the stress field.

It is to be noted that, since the stress field is estimated directly from the acquired surface profile without passing through the determination of geometric coefficients such as roughness coefficients, it is possible to arrive at an estimate of the behavior, taking into account that possible irregularities will not be neutralized by any geometric model whatsoever.

According to advantageous characteristics of the invention, possibly combined:
- the step of determination (or recording) of data characterizing the surface profile of the zone includes a sub-step of measuring the geometric profile of this zone, in practice by any known stylus-type instrument; nevertheless, the use of other techniques may be envisioned, especially purely optical, electrical, acoustic, thermal, the step of recording/determination of data characterizing this profile includes a sub-step of sampling, which makes it possible to reduce the size of storage memory necessary without nevertheless risking complete neutralization of surface irregularities; preferably, this sub-step of sampling is designed so as to reduce the number of data characterizing the surface profile by at least a factor of 10; nevertheless, it is also conceivable to dispense with sampling if the calculation means so permit, the step of determination of data characterizing this profile includes a sub-step of filtering, for example to remove the effect of inclination or geometry of the part (for example, in the case of a cylindrical part, the curvature related to its diameter), the step of determination of data characterizing this profile includes a sub-step of adjustment as a function of the calculation model, which may guarantee that the format imposed by the calculation model is respected, the calculation model to which the data are applied is a finite elements calculation model or variants thereof (XFEM, BARSOOM, etc.), which corresponds to a thoroughly mastered calculation tool; nevertheless, other calculation models may be envisioned, such as, in particular, the other digital methods, such as special digital models, finite or spectral differences, integral methods, the calculation model integrates a thickness of the part; advantageously, this thickness is at least 0.5 mm, preferably at least 1 mm, under the surface of the said zone, which appears to be entirely sufficient for correct estimation of the stress field regardless of the profiles of the surfaces being studied; nevertheless, this thickness may be optimized on a case-by-case basis according to the state of the art, the calculation model determines, for each calculation element (finite element or digital element of the model being used, etc.), stress values along two or three principal axes of the said zone, thus making it possible to obtain a better estimate of the stress field than with a single axis, the model is applied only to at least one non-zero distance from the edges of the zone of the part, for example to at least 1 mm from these edges, in order to avoid the effects of edges (at least to be able to integrate these effects in the calculation model), the quantity characteristic of the fatigue behavior is a maximum stress concentration coefficient, which corresponds to that given by current measuring sequences using both a geometric model and a mechanical model; other quantities such as the stress distribution in the thickness can be obtained easily from the digital model used in the invention.

The objects, characteristics and advantages of the invention become apparent from the following description, given by way of non-limitative example, written with regard to the attached drawings, wherein.

Figure 3:
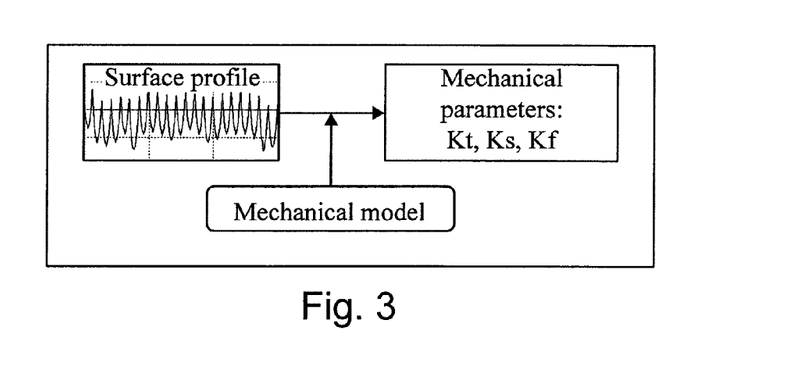
FIG. 3 is a diagram schematically illustrating the steps of the method according to the invention, by analogy with the formalism used in FIG. 1.

According to the invention, a profilometric measurement is used in a mechanical model, without passing through intermediate geometric modeling of the profile, implying determination of roughness coefficients. This measuring sequence is illustrated schematically in FIG. 3: the mechanical model directly uses the recording of the profile in a mechanical model, so as to determine one or more mechanical parameters such as stress concentration coefficients.

Figure 4:
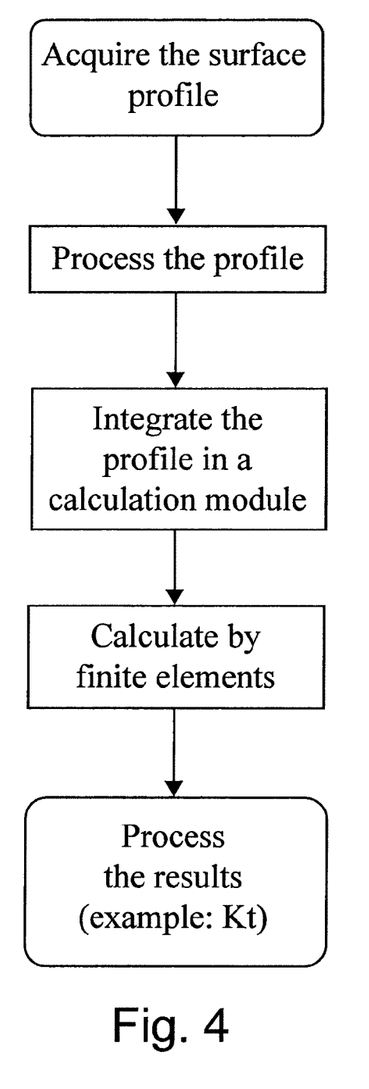
FIG. 4 is a diagram of the implementation of one embodiment of the method of the invention.

The progress of this measuring sequence is represented in FIG. 4, with the following steps:

a step of acquisition of the surface profile by determination (or recording) of data characterizing the surface profile of a chosen zone of the part under consideration, a possible step of processing of the profile (in certain cases, it can be integrated into the acquisition of surface profile data), integration of the profile possibly processed in a calculation model, which is equivalent to applying the data to a calculation model, implementation of the calculation model, so as to estimate the mechanical stress field in the zone whose surface profile has been acquired, processing of the calculation results, so as to deduce from this estimate of the stress field at least one quantity (such as Kt) characteristic of this field and therefore the fatigue behavior of the part under consideration.

The details of these diverse steps can be summarized as follows.

Step 1: Acquiring the surface profile

Figure 5:
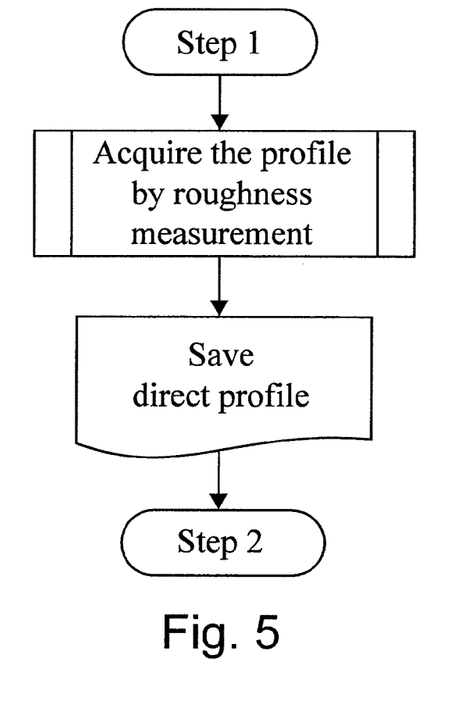
FIG. 5 is a diagram of a first step of implementation of this method.

The geometric state of the surface is measured in this step (see FIG. 5). It is determined by a measuring machine (contact or optical) of any appropriate known type, such as a stylus instrument in conformity with the standard NF-ISO 3274, June 1977, using the arrangements of the standard ISO 4287/1 1984 (E/FR) 1984 already cited hereinabove.

The profile obtained, or in other words either the total profile (direct or gross profile) or the primary profile (in practice, after elimination of the nominal shape of the zone of the analyzed part and application of a low-pass filter if necessary), is recorded digitally and then used in the proposed measuring sequence.

Figure 6:
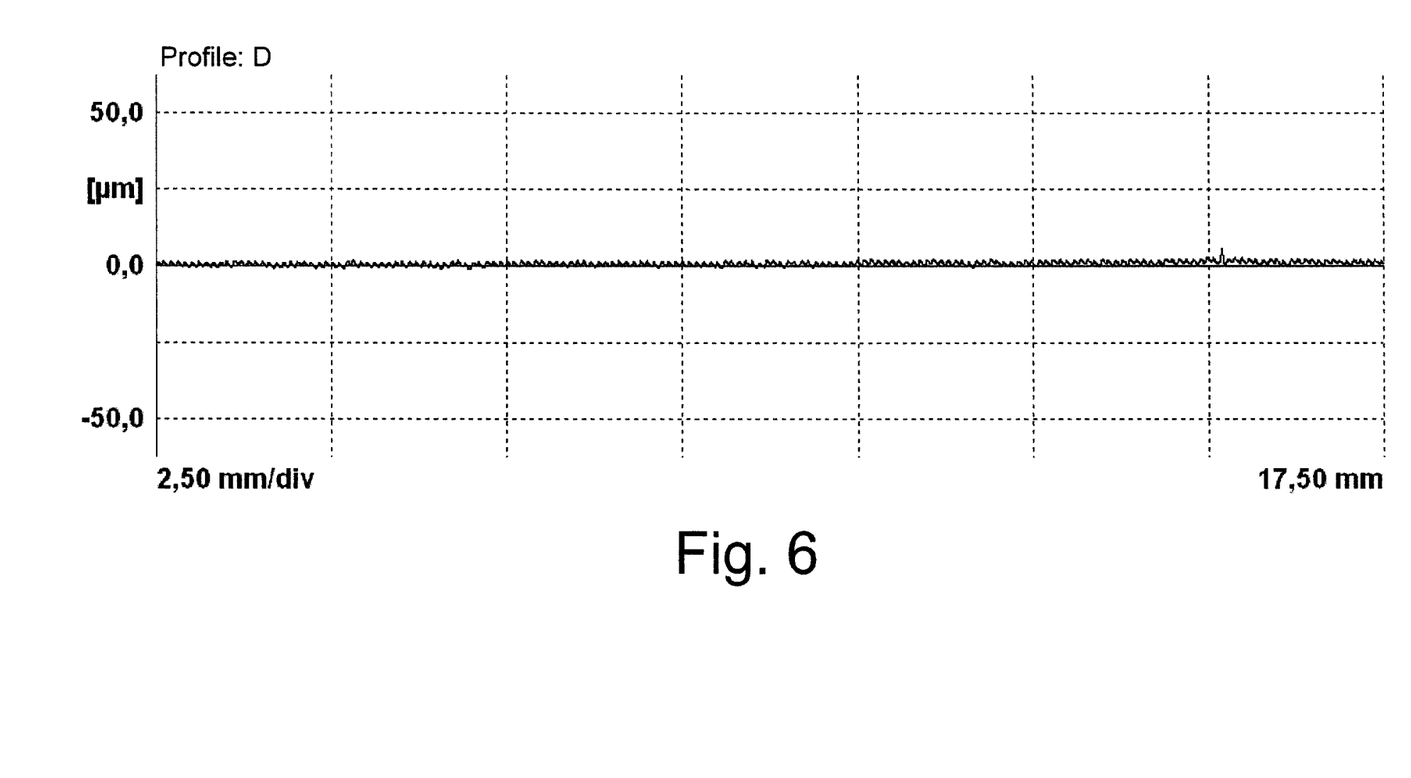
FIG. 6 is a graph showing the profile of a machined test specimen over a length of 17.5 mm.

FIG. 6 shows, as an example, the surface profile acquired for a machined test specimen by a roughness-measuring machine of the "Mahr Perthometer—PKG 120" type.

An evaluation length of 17.50 mm was chosen as reference length for all surface ranges in the example under consideration here. The direct profile obtained without a filter (the total or direct profile) was recorded in ASCII format by an available function suggested by this roughness-measuring machine. This profile is composed of the error of form, the waviness, the periodic or pseudoperiodic roughness (serrations and grooves) and the aperiodic roughness (tears, tool marks and fissures, pits, etc.).

Step 2: Processing the profile

Figure 7:
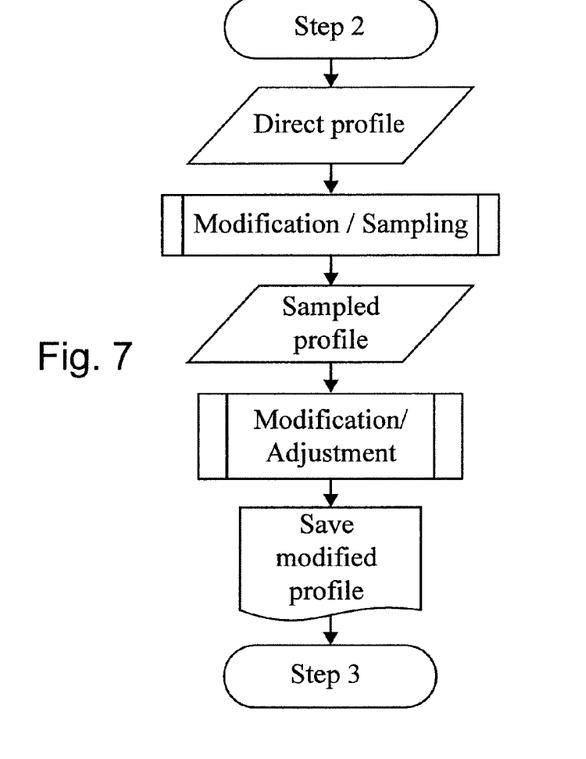
FIG. 7 is a diagram of a second step of implementation of the method.

The profile obtained in the first step is then advantageously sampled, modified and adjusted (see FIG. 7). Sampling has the advantage that it reduces the needed memory size and the calculation time. Several sampling methods are possible, for example with a fixed frequency, with an average neighborhood value, etc. The profile can be modified by different filters to remove undesirable parameters such as inclination. It may be necessary to adjust the result so that this profile can be integrated into the subsequent calculation model.

Figure 8:
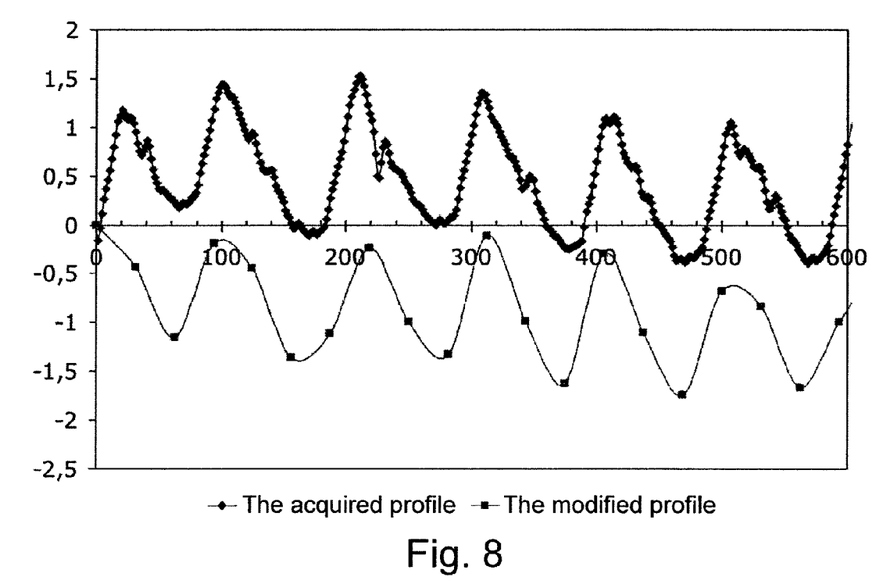
FIG. 8 is a graph showing the acquired profile as well as the modified profile.

FIG. 8 represents, on a much finer scale than in FIG. 6, a detail of the profile acquired during the first step, as well as this same profile after processing. In the example under consideration here, the processing step is performed by calculation software. The sampling method is effected at a fixed frequency chosen so as to reduce the number of points from approximately 11000 points to around 550 points, no other modification being made. The profile heights were then adjusted by suppressing the average of the profile and the arithmetic error of the profile. The first point and/or the last point were imposed in order to respect the condition of having a height equal to zero, with an increment equivalent to the sampled frequency.

The software used in this step was the SCILAB software. Command lines were written and are presented in Annex A. It may be noted on examination of FIG. 8 that the profile obtained is smooth and that certain periodic or pseudoperiodic roughness values as well as aperiodic roughness values have disappeared because of sampling.

Figure 9:
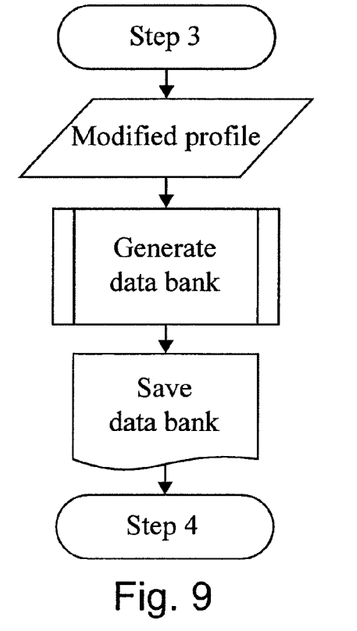
FIG. 9 is a diagram of a third step of implementation of the method.

Step 3: Integrating the profile in a calculation model, in this case a finite elements calculation model The modified profile is then integrated in a calculation model intended to determine the stress field (see FIG. 9). This is advantageously a finite elements calculation model. The integration differs depending on the software chosen. The geometry, the boundary conditions and the hypotheses are fixed appropriately in such a way that the stress field can be calculated.

Figure 10:
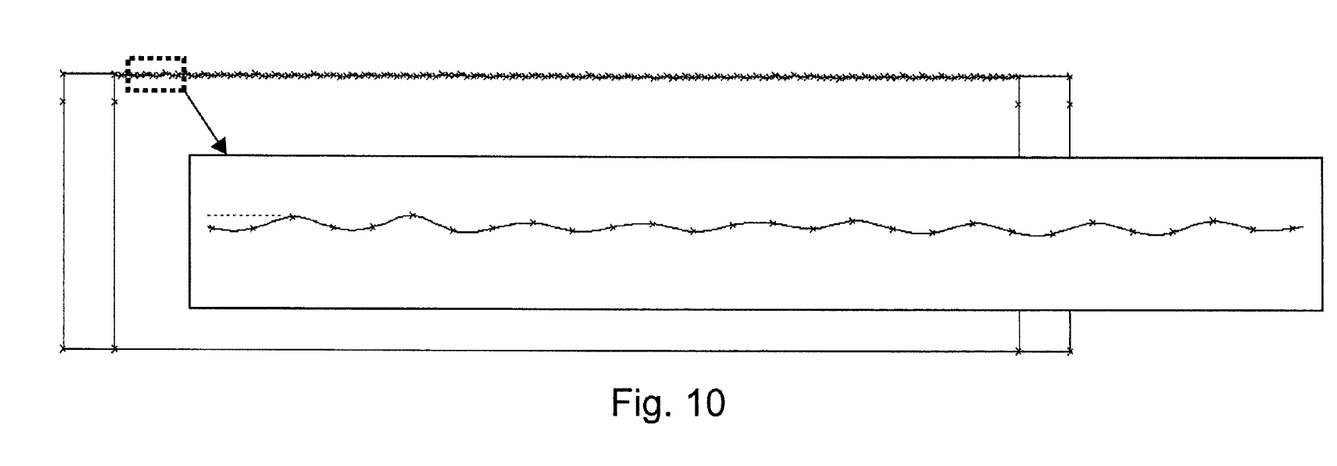
FIG. 10 is a graph showing the modified profile as well as a detail thereof.

The progress from the processed profile (FIG. 10) to the breakdown into finite elements (FIG. 11) was undertaken here by means of the SAMCEF-Asef calculation software. It needs an input database with a specific format generated by a text editor.

Figure 11:
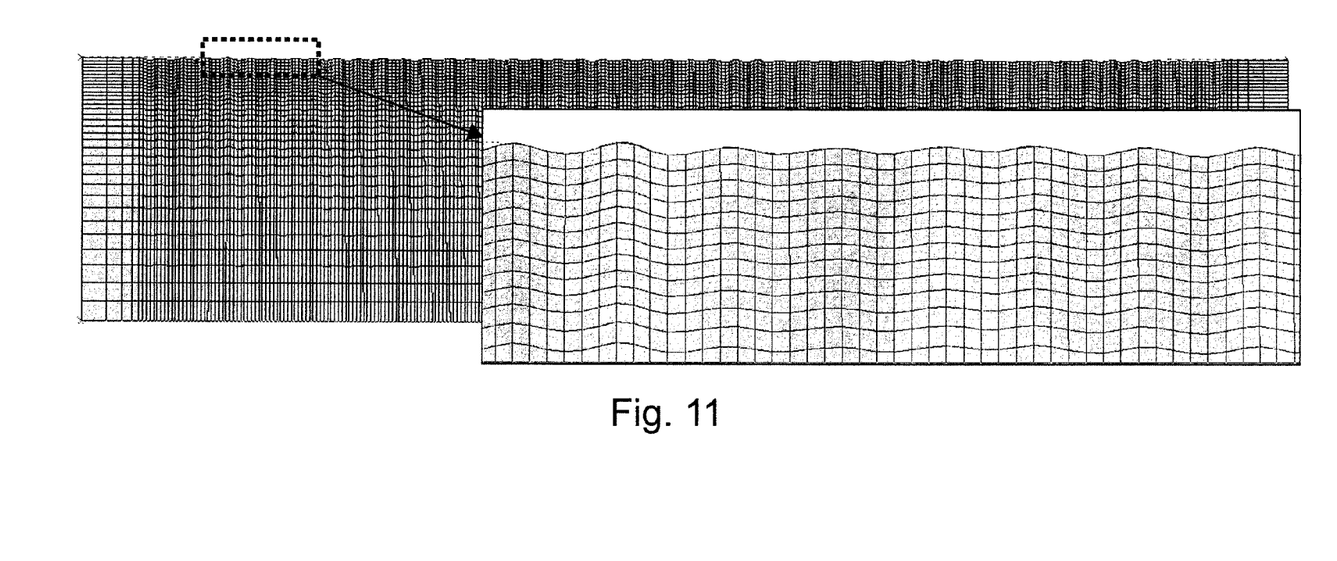
FIG. 11 is a graph showing this modified profile as well as this detail, broken down into finite elements.

In the example considered here, a thickness of 5 mm was taken into consideration by imposing a symmetry plane, which corresponds to an equivalent thickness of 10 mm in the model (on the two sides of the line along which the profile was acquired). The calculation was simplified by the hypothesis of linear elastic behavior and boundary conditions representing uniformly distributed loads. The mesh sizes and number were limited by the available memory zone and the time for the required calculations. To facilitate working in this step, command lines of the SCILAB software were written to generate the calculation file (database) from the processed profile; they are presented in Annex B.

Step 4: Calculation of the stress field, in this case by finite elements

Figure 12:
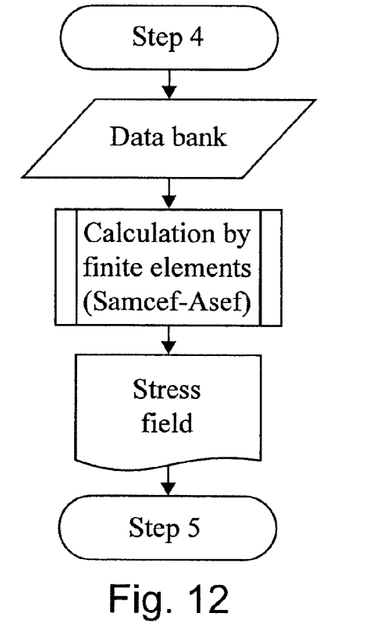
FIG. 12 is a diagram of a fourth step of implementation.

This step (see FIG. 12) is executed by finite elements calculation software. One or more parameters are envisioned in order to represent the stress field obtained in this way.

Figure 13:
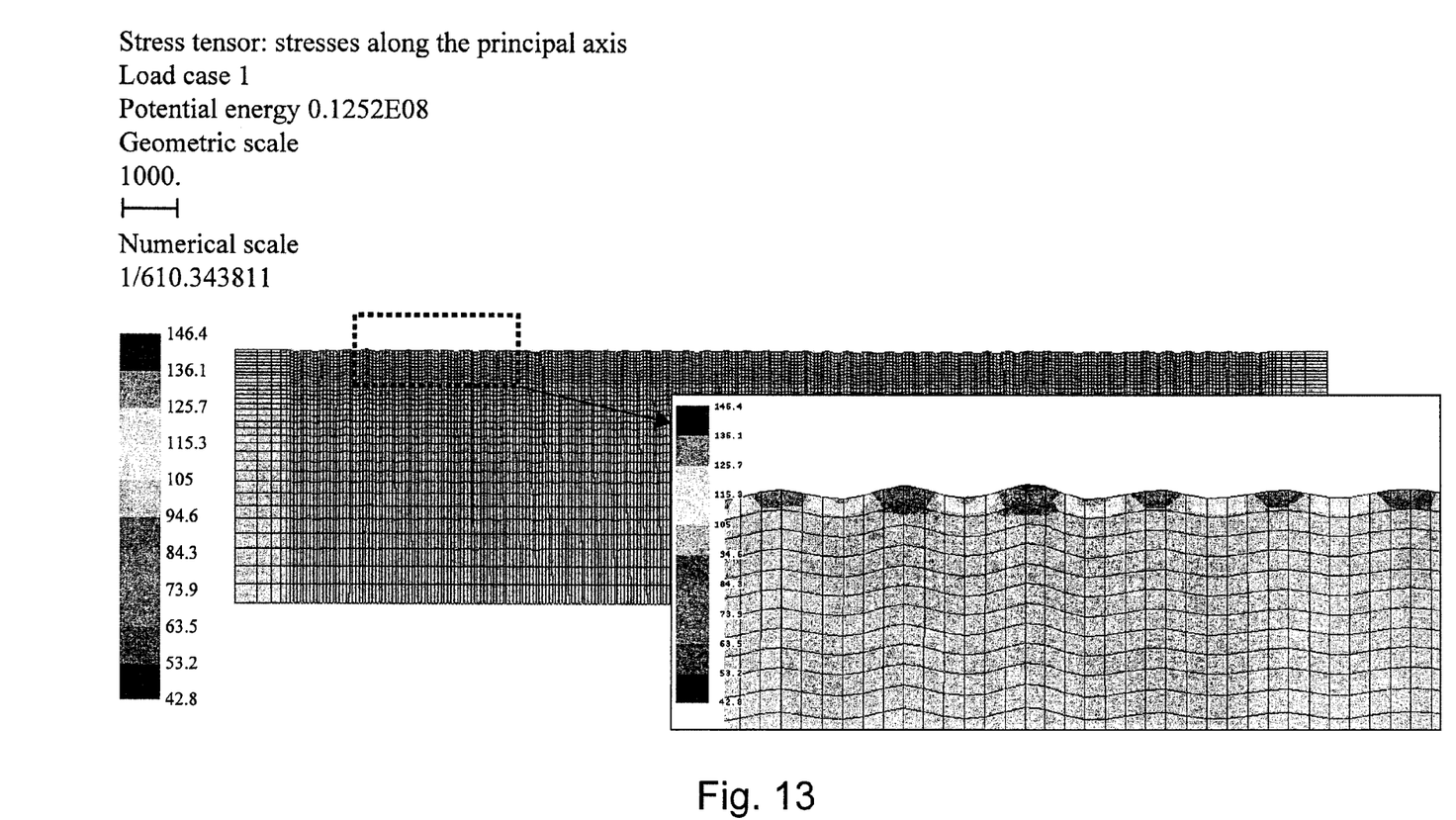
FIG. 13 is a graph representing the local stress field.
Figure 14:
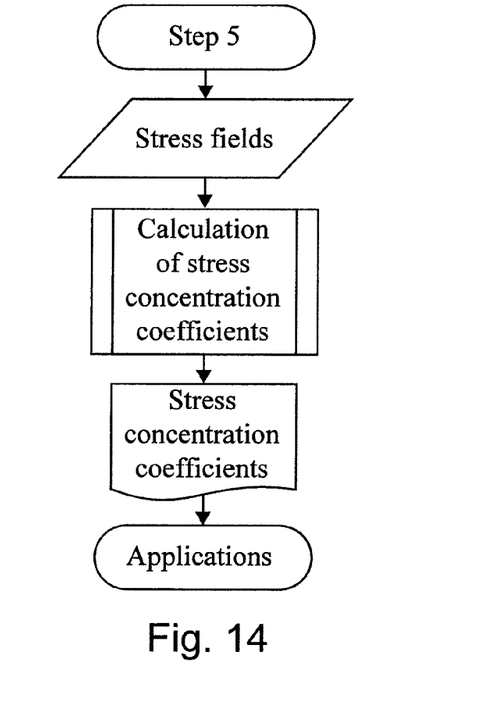
FIG. 14 is a diagram of a fifth step of implementation of the method.

FIG. 13 represents the result obtained by implementing the chosen asef module of the SAMCEF finite elements calculation software (see step 3) in order to calculate the stress field. Only the group of results between the distance of 1 mm and the distance of 16.5 mm was used, so as to eliminate the edge effect (in the zones from 0 to 1 mm and from 16.5 to 17.5 mm), with a depth of 1 mm. They were recorded to be processed in the following step.

Two results (the stresses in the principal axes and the coordinates of the finite element under consideration) were recorded with post-treatment ("post-processing") commands in the database.

Step 5: Processing the results

The data obtained from the step of calculation of the stress field can be processed in diverse ways here with a view to deducing, from the estimate of the stress field, at least one quantity—such as stress concentration coefficients—characteristic of the fatigue behavior of the part under consideration (at least in the examined zone).

By way of example, the stresses of the field estimated in step 4 are divided by the nominal stress, so as to calculate the traditional stress concentration coefficients. One or more parameters characteristic of the influence of the geometric state on the fatigue strength can then be calculated on the basis of these coefficients.

By way of example, the maximum stress concentration coefficients are calculated.

Figure 15:
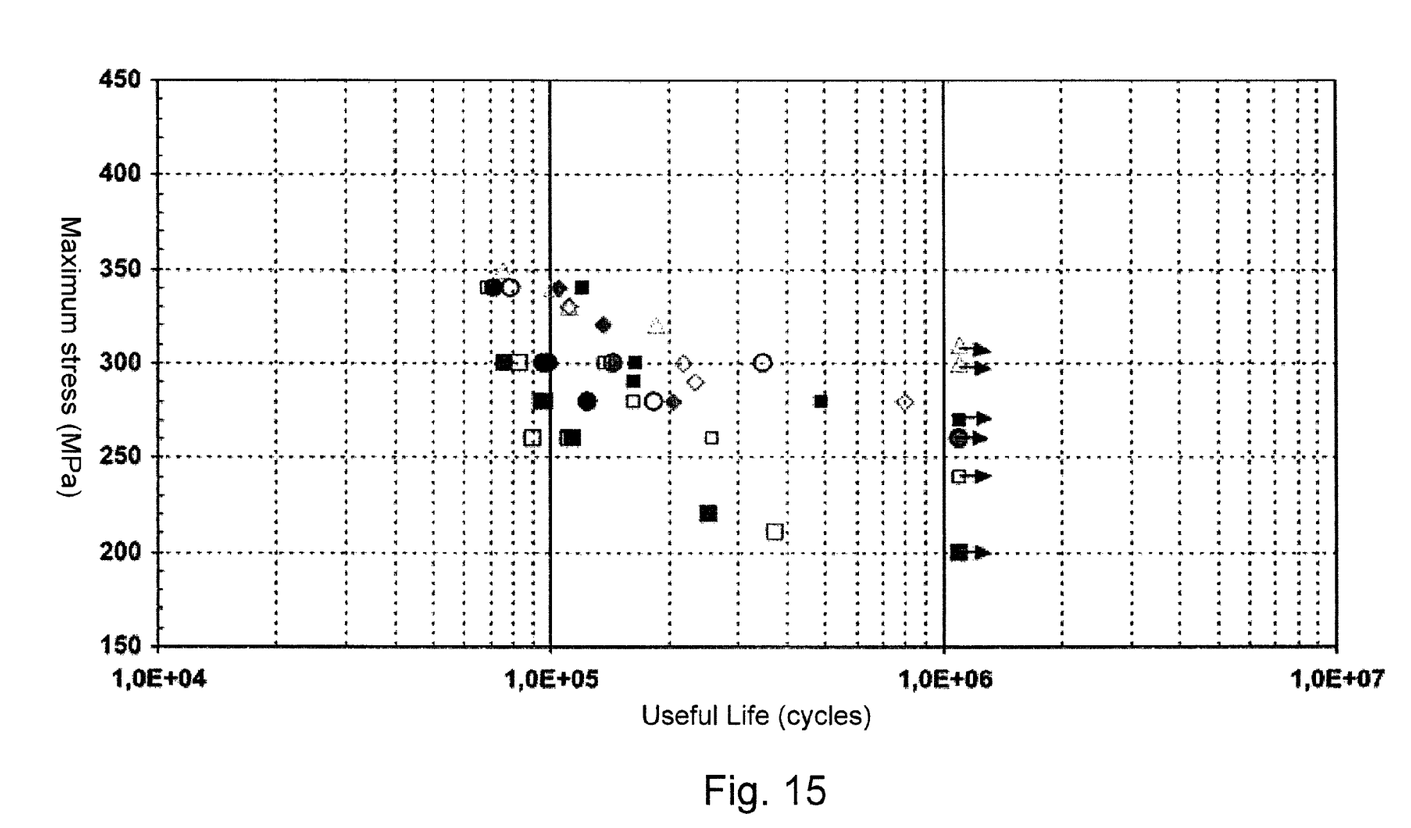
FIG. 15 is a graph showing the Wohler curve obtained for diverse test specimens.
Figure 16:
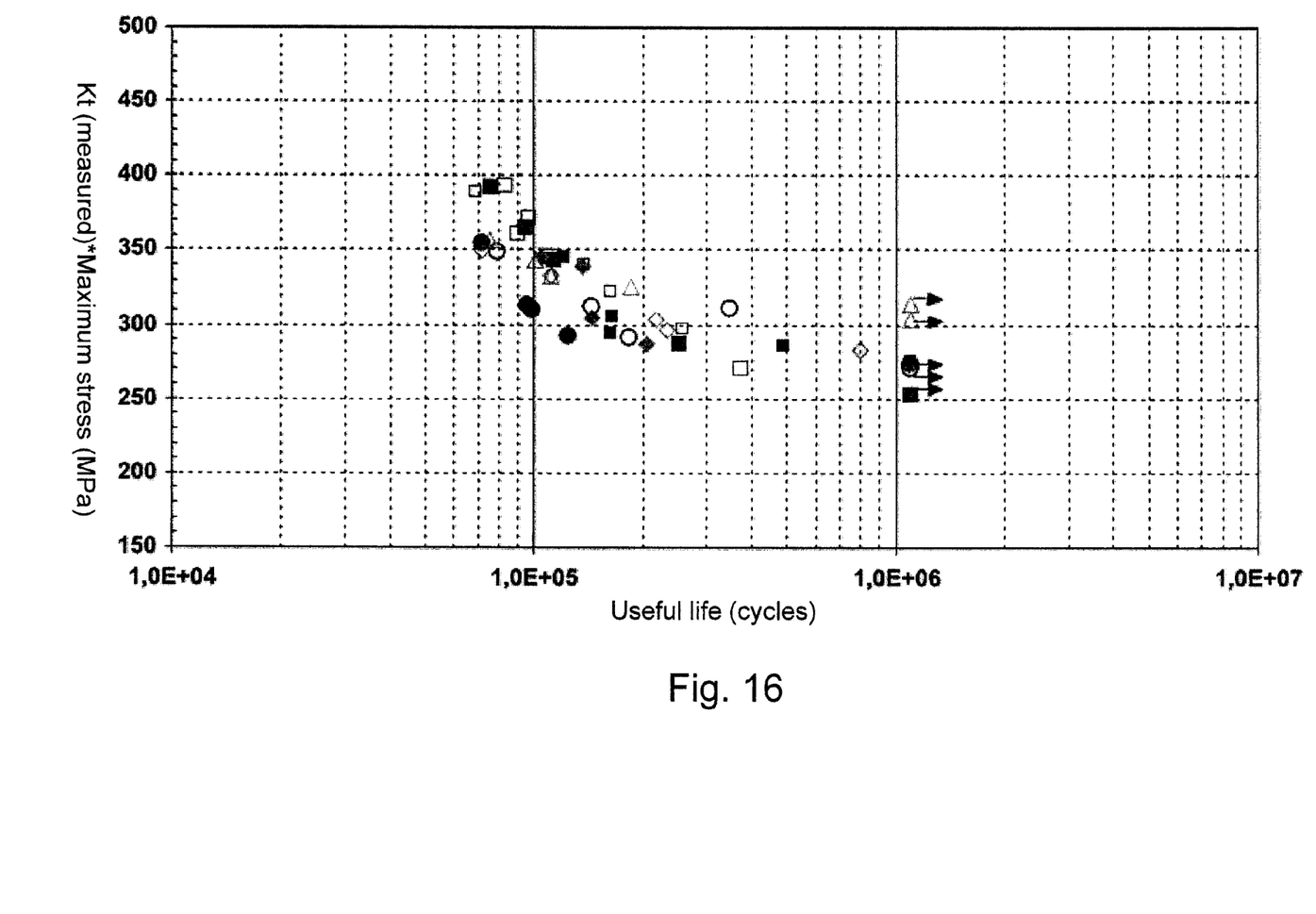
FIG. 16 is a graph showing the Wohler curve obtained for the same test specimens after correction by the stress coefficient determined by the coefficient obtained at the end of the fifth step.

An example of use of the results obtained is presented in FIGS. 15 and 16: the fatigue test results, represented by the Wohler curve of FIG. 15, were corrected by the maximum stress concentration factors Kt obtained (see FIG. 16). By comparing these FIGS. 15 and 16, it is seen that the differences between the different surface states are largely attenuated by correcting (multiplying) with the measured Kt values.

It is therefore established that the proposed measuring sequence is capable of furnishing indicators of quality of surface states of parts intended to be subjected to mechanical loading. This measuring sequence has the advantage that it does not pass through geometric parameters and therefore does not necessitate a priori knowledge of the influence of a particular type or irregularity over the useful life of the part.

---

Annex A: The Scilab command lines for effecting the operations of step 2

```
//Scilab
//Step 2 - Sampling and modifying the profile
//         on the basis of a profile measured by Mahr-PGK120
(roughness measurement)
//on 01 June 2005
clear
roughnessfile = 'profile_direct.TXT';
sample=550; //Approximate sampling number of the profile
[fr,er]=mopen(roughnessfile,'r');
if (er===0) then
    //Import the profile file
    mprintf('Import '%s'\n',roughnessfile)
    roughness=tlist(['Point',mfscanf(fr,'%s %s %s')]);
    ind=0;
    err=meof(fr);
    while err===0,
        l=mfscanf(fr,'%f %c');
```

| Annex A: The Scilab command lines for effecting the operations of step 2 |
|---|
| ```
        if 1(l) ===[ ] then break, end;
        ind = ind+1;
        resi = 0;
        pwr = 1;
        r = mfscanf(fr,'%c');
        while (r<> code2str(-40))&(r <> code2str(110)),
            resi = resi + str2code(r)/(10**pwr);
    pwr = pwr+1;
            r = mfscanf(fr,'%c');
        end,
        roughness(2)(ind)=1(l)+resi;
        r = mfscanf(fr,'%c');
    if(r==='-') then
        dir = -1;
        l=mfscanf(fr,'%f%c');
    else
        dir = 1;
        l = 0;
        while (r <> ','),
            l = l*10+str2code(r);
            r = mfscanf(fr,'%c');
        end,
    end,
        resi = 0;
        pwr = 1;
        r = mfscanf(fr,'%c');
        while (r<> code2str(-40))&(r <> code2str(110)),
            resi = resi + str2code(r)/(10**pwr);
``` |

| Annex A: The Scilab command lines for effecting the operations of step 2 |
|---|
| ```
    pwr = pwr+1;
            r = mfscanf(fr,'%c');
        end,
        roughness(4)(ind)=dir*(1(l)+resi);
        err=meof(fr);
    end;
    mclose(fr);
    //Sampling
    j=1;
    sample=round(ind/sample);
    for i = 1:ind
        if modulo(i,sample) === 0 then
            profile(j,1)=j+1;
            profile(j,2)=roughness(2)(i);
            profile(j,3)=roughness(4)(i);
            j=j+1;
        end,
    end;
    //Modify the profile
    average = mean(profile(:,3));
    arith = mad(profile(:,3));
    profile(:,3)=profile(:,3)-(average+arith);
    profile(j,1)=j+1;
    profile(j,2)=profile(j-1,2)+profile(j-1,2)-profile(j-2,2));
    profile(j,3)= 0;
    save('profile.dat',profile);
end;
``` |

| Annex B: The Scilab command lines for effecting the operations of step 3 |
|---|
| ```
//Scilab
//Step 3 - Generate bankfile for finite elements calculation (Samcef-asef)
//on 01 June 2005
clear
bankfile = 'test.dat';
dquote = ascii(34);
fd=mopen('bankfile,'w');
load('profile.dat');
// Generate bank file for calculation by Samcef(Asef)
// Preliminary
mfprintf(fd,'\!************************************************** \n...
\!* Model EFM-2D                   *\n...
\!* Obj:Calculate the stress concentration *\n...
\!* Material: Aluminum-elastic            *\n...
\!* Model: Measured surface               *\n...
\!* Hypothesis: Plane deformation         *\n...
\!* Mesh: Direct transfinite              *\n...
\!* CL: tension&tension each end     *\n...
\!************************************************** \n...
\!* Author:                       *\n...
\!* the %s                        *\n...
\!************************************************** \n...
\!************************************************** \n',date( ))
// Abbreviation of the variables
mfprintf(fd,'.del.*\n...
\n...
\! \n...
\! Abbreviation of the parameters \n...
\!============================================================ \n...
\! \n...
\! General geometry \n...
\!-------------------------------------------- \n...
ABBRE '\\thick'       '5000'    \t\! Thickness \(um\) \n...
ABBRE '\\sec2'        '1000'    \t\! Smooth surface (um) \n...
ABBRE '\\mf_y'         '500'    \t\! Thickness of fine mesh zone (um) \n...
ABBRE '\\lm'         '%0.2f'    \t\! Profile length \n...
\! \n...
\! Characteristic of the material \n...
\!-------------------------------------------- \n...
ABBRE '\\E_alu'     '70000'    \! Young's modulus of aluminum \(N/mm;MPa\) \n...
ABBRE '\\poi_alu'    '0.33'    \! Poisson's coefficient \n...
\! \n...
``` |

-continued

Annex B: The Scilab command lines for effecting the operations of step 3

```
\! Number of elements \n...
\!---------------------------------------------- \n...
ABBRE '\\NE-surf'        '500'         \t\! On the profile \n...
ABBRE '\\NE_sec2'                '(\\sec2:\\lm:\\NE_surf))'   \t\! Smooth surface \n...
ABBRE '\\NE_fineY'    '(\\mf_y:\\lm:\\NE_surf))' \t\! Fine mesh zone \n...
ABBRE '\\NE_coarseY' '((\\thick-\\mf_y):\(\\lm:NE_surf))'   \n',profile(j,2))
// Geometry
mfprintf(fd,'\l \n...
\! A. Geometry \n...
\!---------------------------------------------- \n...
\! A.1. 2D geometry \n...
\!---------------------------------------------- \n...
.Point \n...
\! Coordinates of the profile \n')
mfprintf(fd,'\n')
mfprintf(fd,'I %4i \t X %9.2f\t Y%9.4f\n',1,0,0)
mfprintf(fd,'I %4i \t X %9.2f\t Y%9.4f\n',profile)
mfprintf(fd,'\l \n...
.Spline \n...
I 1 Point 1 at %i \n...
\n...
.Point \n...
     i 8001 x 0               y −(\\mf_y) \n...
     i 8002 Rx 0              y −(\\thick) \n...
     i 8003 x −(\\sec2)       y 0 \n...
     i 8004 Rx 0              y −(\\mf_y) \n...
     i 8005 Rx 0              y −(\\thick) \n...
     i 8007 x (\\lm)          y −(\\mf_y) \n...
     i 8008 Rx 0              y −(\\thick) \n...
     i 8009 x −(\\lm+\\sec2)  y 0 \n...
     i 8110 Rx 0              y −(\\mf_y) \n...
     i 8005 Rx 0              y −(\\thick) \n...
\!n...
.STRAIGHT LINE \n...
     i 103 Point 1 8001 8002 \n...
     i 105 Point %; 8007 8008 \n...
     i 107 Point 8003 to 8005 \n...
     i 109 Point 8009 to 8011 \n...
     i 111 Point 8003 1 \n...
     i 112 Point %; 8009 \n...
     i 113 Point 8005 8002 8008 8011 \n...
\! Loading line \n...
     i 121 Point 8003 8005 \! A left \n...
     i 122 Point 8009 8011 \! A right \n...
     i 123 Point 8005 8011 \! Below \n',j+1,j+1,j+1)
// Mesh
mfprintf(fd,'\l \n...
\! \n...
\! A.2. Mesh \n...
\!---------------------------------------------- \n...
.CONTOUR \n...
     i 1 Line 105 106 114 104 103 1 \n...
     i 2 Line 103 104 113 108 107 111 \n...
     i 3 Line 105 106 115 110 109 112 \n...
\n...
.Auto domain \n...
\n...
.GEN \n...
\! Horizontal mesh (X axis) \n...
     modify Line 111 113 \t element (\\NE_sec2:3) distribute 3 6 \n...
     modify Line 112 115 \t element (\\NE_sec2:3) distribute 2 6 \n...
     modify Line 1 \t element (\\NE_surf) \n...
     modify Line 114 \t element (\\NE_surf) \n...
\! Vertical mesh (Y axis) \...
     modify Line 107 103 105 109 \t element (\\NE_fineY) \n...
     modify Line 108 104 106 110 \t element (\\NE_coarseY) distribute 2 6 \n...
\n...
\! Automatic mesh \n...
deg 1 \n...
     c1 1 c2 105 106 c3 114 c4 104 103 \n...
     mesh 1 transfinite \n...
     c1 111 c2 103 104 c3 113 c4 108 107 \n...
     mesh 2 transfinite \n...
     c1 112 c2 109 110 c3 115 c4 106 105 \n...
     mesh 3 transfinite \n...
\n...
\! \n...
\! A.3. Mesh modifications \n...
```

| Annex B: The Scilab command lines for effecting the operations of step 3 |
|---|

```
\!-------------------------------------------- \n...
\n')
// Hypothesis and group selection
mfprintf(fd,'\! \n...
\! Hypothesis and material \n...
\!================================================================ \n...
\n...
.MAT \n...
    I 1 name 'Alu-elastic' \n...
    Beha %cElastic%c \n...
    Yt(\\E__Alu) \n...
    Nt(\\Poi__Alu) \n...
\n...
.AEL \n...
    ATTRIBUTE 1 to 3 MAT 1 \n...
\n...
.hyp DEFO PLAN \n...
\! Selection of groups \n...
.SEL \n...
\n...
    Group 1 nodes name %cResult__zone%c \n...
        BOX STRUCTURE $ \n...
            X1 (1000) XS (\\lm-1000) $ \n...
            Y1 (100) YS (-1000) $ \n...
            Z1 -(1) ZS (1) \n...
\n',dquote,dquote,dquote,dquote)
// Boundary conditions
mfprintf(fd,'\! \n...
\! C. Boundary conditions \n...
\!================================================================ \n...
.CLM \n...
\! Load case 1 'tension' \n...
    load line 122 con    100 compo 1 nc 1 \n...
    Fix line 121 compo 1 \n...
    Fix line 123 compo 2 4 6 \n...
\n...
\! General data \n...
\!------------- \n...
.sam nop5 nop6 1 \n...
.fin 1 \n')
// Post-processing
mfprintf(ft1, \!================================================================ \n...
.Post & \n...
.Del.* \n...
.doc db %ctest%c__as%c \n...
.des \n...
Disc -1 \n...
trace mode = %cresult.txt%c \n...
code 1411 comp 1 \n...
group 2 \n...
list \n...
trace mode 0 \n...
trace mode =%cnodes.txt%c \n...
.node load group 2 \n...
list \n...
trace mode 0 \n...
.stop \n'...
,dquote,dquote,dquote,dquote,dquote,dquote,dquote,dquote)
mclose(fd);
mprintf('Exporter '%s' \n',bankfile)
```

The invention claimed is:

1. A method for characterizing a fatigue strength of a part on a basis of the part's surface state, the method comprising:

measuring, by a measuring device, geometric features which indicate a surface profile of a zone in which the fatigue strength of the part is to be determined, the surface profile indicating respective depths and dimensions of surface features across the zone of the part;

recording, in a memory, geometric features which indicate the surface profile of the part that is acquired by the measuring device;

applying, by a calculation unit including a processor, the geometric features to a calculation model so as to formulate an estimate of a mechanical stress field in the zone of the part, the mechanical stress field is estimated directly from the acquired surface profile without determining geometrical coefficients; and determining, in the calculation unit, from the estimate of the mechanical stress field at least one quantity characteristic of a fatigue behavior of the part.

2. A method according to claim 1, wherein the recording of the surface profile of the zone includes a sub-step of measuring the geometric features of the zone.

3. A method according to claim 2, wherein the recording of the surface profile includes a sub-step of sampling.

4. A method according to claim 3, wherein the sub-step of sampling reduces a number of data characterizing the surface profile by at least a factor of 10.

5. A method according to claim 2, wherein the recording of the surface profile includes a sub-step of filtering.

6. A method according to claim 2, wherein the step of recording of geometric features characterizing the surface profile includes a sub-step of adjustment as a function of the calculation model.

7. A method according to claim 1, wherein the calculation model to which the geometric features are applied is a finite elements calculation model.

8. A method according to claim 7, wherein the calculation model integrates a thickness of the part of at least 0.5 mm under the surface of the zone.

9. A method according to claim 1, wherein the calculation model determines, for each calculation element, stress values along two or three principal axes of the zone.

10. A method according to claim 1, wherein the model is applied only to at least one non-zero distance from the edges of the zone of the part.

11. A method according to claim 1, wherein the at least one quantity characteristic of the fatigue behavior is a maximum stress concentration coefficient.

12. A method according to claim 1, further comprising:
modifying the surface profile by adjusting profile heights of the part by suppressing an average of the profile and arithmetic error of the profile.

\* \* \* \* \*